United States Patent [19]

Watanabe et al.

[11] Patent Number: 4,672,109
[45] Date of Patent: Jun. 9, 1987

[54] METHOD FOR SELECTIVE METHYLATION OF ERYTHROMYCIN A DERIVATIVES

[75] Inventors: Yoshiaki Watanabe, Kodaira; Shigeo Morimoto; Masami Goi, both of Kitakatsushika; Morihiro Mitsukuchi, Omiya; Takashi Adachi, Kuki; Jozi Nakagami, Saitama; Toshifumi Asaka, Ageo; Tadashi Eguchi, Omiya; Kaoru Sota, Tokorozawa, all of Japan

[73] Assignee: Taisho Pharmaceutical Co., Ltd., Tokyo, Japan

[21] Appl. No.: 720,383

[22] Filed: Apr. 5, 1985

[30] Foreign Application Priority Data

Apr. 6, 1984 [JP] Japan ................... 59-68509

[51] Int. Cl.$^4$ ........................................... C07H 17/08
[52] U.S. Cl. ..................................... 536/7.2; 536/7.5
[58] Field of Search ............................. 536/7.2, 18.5

[56] References Cited

U.S. PATENT DOCUMENTS

| 4,331,803 | 5/1982 | Watanabe et al. | 536/7.2 |
| 4,476,298 | 10/1984 | Morimoto et al. | 536/7.2 |
| 4,496,717 | 1/1985 | Adachi et al. | 536/7.2 |

FOREIGN PATENT DOCUMENTS 1100504  1/1968  United Kingdom ............. 536/7.2

Primary Examiner—Johnnie R. Brown
Assistant Examiner—Elli Peselev
Attorney, Agent, or Firm—Cushman, Darby & Cushman

[57] ABSTRACT

A method for the selective methylation of a hydroxy group at the 6-position of an erythromycin A derivative which comprises converting an erythromycin A derivative into an erythromycin A 9-oxime derivative, and reacting the resulting ethythromycin A 9-oxime derivative with an methylating agent.

8 Claims, No Drawings

METHOD FOR SELECTIVE METHYLATION OF ERYTHROMYCIN A DERIVATIVES

BACKGROUND OF THE INVENTION

1. The Field of the Invention

The present invention relates to a method for the selective methylation of a hydroxy group at the 6-position of erythromycin A derivatives.

2. Description of the Prior Art

6-O-Methylerythromycins are useful as anti-bacterial agents or intermediates for the synthesis of the anti-bacterial agents. For example, 6-O-methylerythromycin A is not only stable in the acidic condition but also has a strong anti-bacterial activity when compared with erythromycin A. Especially, this compound shows an excellent effect for treatment of infections by oral administration, and therefore it is a useful anti-bacterial agent.

However, since erythromycin A has many hydroxy groups as shown by the following formula (I), it is difficult to methylate only a specific hydroxy group at the 6-position selectively.

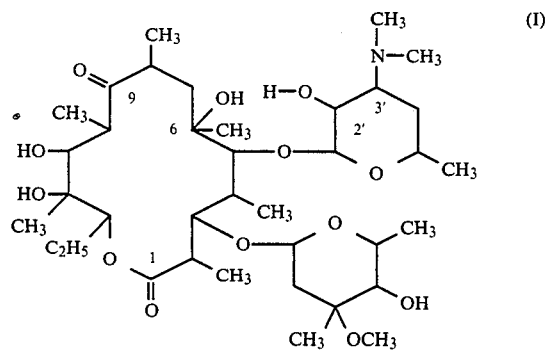
(I)

As the previous method for methylating the hydroxy group at the 6-position of erythromycin A, there is known a method for preparing a 6-O-methylerythromycin A derivative which comprises reacting an erythromycin A derivative, substituted with benzyloxycarbonyl groups at a hydrogen atom of the 2'-hydroxy group and a methyl group of the 3'-dimethylamino group, with a methylating agent in the presence of a base in a polar aprotic solvent in order to methylate the hydroxy group at the 6-position (U.S. Pat. No. 4,331,803). In this method, however, are obtained various kinds of the compounds which are methylated at hydroxy groups at any other than the 6-position together with the 6-O-methyl form, and therefore, this method requires the complicated procedure for purification of the objective 6-O-methyl form, and the yield of the 6-O-methyl form is low.

SUMMARY OF THE INVENTION

According to the present invention, there is provided a method for the selective methylation of a hydroxy group at the 6-position of an erythyromycin A derivative which comprises converting an erythromycin A derivative into an erythromycin A 9-oxime derivative, and reacting the resulting erythromycin A 9-oxime derivative with an methylating agent.

DETAILED DESCRIPTION OF THE INVENTION

The term "erythromycin A derivative" means erythromycin A having no substituent group or having conventional substituent groups, in organic synthesis, in place of a hydrogen atom of the 2'-hydroxy group and/or a methyl group of the 3'-dimethylamino group which is prepared according to the conventional manner. The term "erythromycin A 9-oxime derivative" means an erythromycin A derivative having at the 9-position the general formula

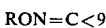
(II)

wherein R is a hydrogen atom or a substituent group such as a lower alkyl group (e.g., a methyl group, an ethyl group, a n-propyl group, an isopropyl group and the like) a lower alkenyl group (e.g., an allyl group and the like), an aryl substituted methyl group (e.g., a benzyl group, a p-methoxybenzyl group, a p-chlorobenzyl group, a m-chlorobenzyl group, an o-chlorobenzyl group, a 2,4-dichlorobenzyl group, a p-bromobenzyl group, a m-nitrobenzyl group, a p-nitrobenzyl group, a benzhydryl group, a trityl group, a 1-naphthylmethyl group and the like), a substituted oxyalkyl group [e.g., a methoxymethyl group, a (2-methoxyethoxy)methyl group, a (2-ethoxyethoxy)methyl group, a (2-methylpropoxy)methyl group, a 2-chloroethoxymethyl group, a 2,2,2-trichloroethoxymethyl group, a 2-ethoxyethyl group, a benzyloxymethyl group, a p-chlorophenoxyethyl group and the like], a substituted alkyl group [e.g., a (1,3-dioxolan-2-yl)methyl group, 3,3-dimethyl-2-oxobutyl group and the like] or a substituted thiomethyl group (e.g., a methylthiomethyl group, an ethylthiomethyl group, a phenylthiomethyl group and the like).

In an embodiment of the present invention, an erythromycin A derivative is converted into an erythromycin A 9-oxime derivative having the formula (II) wherein R is a hydrogen atom according to a known method (e.g., U.K. Pat. No. 1,100,504) or the method similar to the above. The resulting erythromycin A 9-oxime derivative having the formula (II) wherein R is a hydrogen atom is reacted with a compound of R'X (wherein R' is R other than a hydrogen atom), or erythromycin A is reacted with an O-substituted hydroxylamine to convert into the erythromycin A 9-oxime derivative having the formula (II) wherein R is other than a hydrogen atom according to a known method (e.g, U.S. Pat. No. 4,349,545) or the method similar to the above. Examples of the compound of R'X are lower alkyl halides (e.g., methyl iodide, ethyl iodide, n-propyl iodide, isopropyl bromide and the like), lower alkenyl halides (e.g., allyl bromide and the like), aryl substituted methyl halides (e.g., benzyl chloride, p-methoxybenzyl chloride, p-chlorobenzyl chloride, m-chlorobenzyl chloride, o-chlorobenzyl chloride, 2,4-dichlorobenzyl chloride, p-bromobenzyl bromide, m-nitrobenzyl chloride, p-nitrobenzyl chloride, benzhydryl chloride, trityl chloride, 1-naphthylmethyl chloride and the like), substituted oxyalkyl halides [e.g., methoxymethyl chloride, (2-methoxyethoxy)methyl chloride, (2-ethoxyethoxy)methyl chloride, (2-methylpropoxy)methyl chloride, 2-chloroethoxymethyl chloride, 2,2,2-trichloroethoxymethyl chloride, 2-ethoxyethyl chloride, benzyloxymethyl chloride, p-chlorophenoxyethyl chloride and the like], substituted alkyl halides [e.g., (1,3-dioxolan-2-yl)methyl chloride, 3,3-dimethyl-2-oxobutyl chloride and the like], nitrile compounds (e.g., bromoacetonitrile, β-chloropropionitrile and the like), or substituted thiomethyl halides (e.g., methylthiomethyl chloride, ethylthiomethyl chloride, phenylthiomethyl chloride and the like).

An erythromycin A 9-oxime derivative is dissolved in a solvent, a methylating agent and a base are added, and the mixture is stirred at −15° to 40° C., preferably 0° C. to room temperature, for 0.5 to 6 hours to give a 6-O-methylerythromycin A 9-oxime derivative. While checking the progress of the reaction by means of thin layer chromatography or high speed liquid chromatography, the reaction is carried out until the presence of the erythromycin A 9-oxime derivative is scarecely detected. In order to obtain the 6-O-methyl-erythromycin A 9-oxime derivative thus prepared, after completion of the reaction, the reaction solution is added to water. The crystals of the 6-O-methylerythromycin A 9-oxime derivative which precipitate are filtered. Alternatively, the reaction solution is extracted with a non-hydrophilic organic solvent. If necessary, the purification is further carried out by a silica gel column chromatography or recrystallization.

When used the erythromycin A 9-oxime derivative having the formula (II) wherein R is a hydrogen atom for methylation, there is obtained the 6-O-methylerythromycin A 9-oxime derivative having the formula (II) wherein R is a methyl group.

Preferred examples of the solvents used in the methylation are polar aprotic solvents such as dimethyl sulfoxide, N,N-dimethylformamide, hexamethylphosphoric triamide, a mixture consisting of two or more of these solvents, or a mixture consisting of one of these solvents and tetrahydrofuran, 1,2-dimethoxyethane and the like. Most preferred solvents are a mixture of dimethyl sulfoxide and tetrahydrofuran (1:1), a mixture of dimethyl sulfoxide and 1,2-dimethoxyethane (1:1) or N,N-dimethylformamide.

Examples of the methylating agent are methyl halides such as methyl iodide, methyl bromide and the like; dimethyl sulfate, methyl p-toluenesulfonate, methyl methanesulfonate and the like.

Although 1.0 to 10 molar equivalents of the methylating agent can be used per mole of the erythromycin A 9-oxime derivative, it is usually sufficient to use 1.0 to 2.6 molar equivalents of it.

Examples of the base are potassium hydroxide, sodium hydroxide, sodium hydride, potassium hydride and the like. 1.0 to 1.7 molar equivalents, preferably 1.0 to 1.2 molar equivalents of the base can be used per mole of the erythromycin A 9-oxime derivative. The base is added in one or several portions.

The presence of the O-methyl group at the 6-position of the 6-O-methylerythromycin A 9-oxime derivative can be detected by the characteristic peak in the NMR spectrum.

The 6-O-methylerythromycin A 9-oxime derivatives and the erythromycin A 9-oxime derivatives may exist in the syn-form, anti-form or a mixture of the syn- and anti-form.

Examples of the substituent group in place of a methyl group of the 3′-dimethylamino group of the erythromycin A derivative used as the starting material are alkoxycarbonyl groups (e.g., a methoxycarbonyl group, an ethoxycarbonyl group, an isopropoxycarbonyl group, a n-propoxycarbonyl group, an n-butyloxycarbonyl group, an isobutyloxycarbonyl group, a sec-butyloxycarbonyl group, t-butyloxycarbonyl group, a 2-ethylhexyloxycarbonyl group, a cyclohexyloxycarbonyl group, a menthyloxycarbonyl group and the like), alkoxyalkoxycarbonyl groups (e.g., a methoxymethoxycarbonyl group, an ethoxymethoxycarbonyl group, a 2-methoxyethoxycarbonyl group, a 2-ethoxyethylcarbonyl group, a 2-ethoxyethoxycarbonyl group, a 2-butoxyethoxycarbonyl group, a 2-methoxyethoxymethoxycarbonyl group and the like), haloalkoxycarbonyl groups (e.g., a 2-chloroethoxycarbonyl group, a 2-chloroethoxycarbonyl group, a 2,2,2-trichloroethoxycarbonyl group and the like), unsaturated alkoxycarbonyl groups (e.g., an allyloxycarbonyl group, a propargyloxycarbonyl group, a 2-butenoxycarbonyl group, a 3-methyl-2-butenoxycarbonyl group and the like), substituted benzyloxycarbonyl groups (e.g., a benzyloxycarbonyl group, a p-methylbenzyloxycarbonyl group, a p-methoxybenzyloxycarbonyl group, a p-nitrobenzyloxycarbonyl group, a 2,4-dinitrobenzyloxycarbonyl group, a 3,5-dimethylbenzyloxycarbonyl group, a p-chlorobenzyloxycarbonyl group, a p-bromobenzyloxycarbonyl group and the like) and substituted phenoxycarbonyl groups (e.g., a phenoxycarbonyl group, a p-nitrophenoxycarbonyl group, an o-nitrophenoxycarbonyl group, a 2,4-dinitrophenoxycarbonyl group, a p-methylphenoxycarbonyl group, a m-methylphenoxycarbonyl group, an o-bromophenoxycarbonyl group, a 3,5-dimethylphenoxycarbonyl group, a p-chlorophenoxycarbonyl group, a 2-chloro-4-nitrophenoxycarbonyl group and the like). Examples of the substituent group in place of a hydrogen atom of the 2′-hydroxy group are the carbonyl groups as described above, acyl groups used in usual organic synthesis (e.g., lower alkyl monocarbonyl groups such as an acetyl group, a propionyl group, a butyryl group, an isobutyryl group and the like; lower alkenyl monocarbonyl groups such as an acryloxyl group, a methacryloxy group and the like; lower alkoxycarbonylalkylcarbonyl groups such as a methoxycarbonylmethylcarbonyl group, an ethoxycarbonylmethylcarbonyl group, an ethoxycarbonylethylcarbonyl group and the like; arylcarbonyl groups such as a benzoyl group, a p-methoxybenzoyl group, a 3,4,5-trimethoxybenzoyl group, a p-chlorobenzoyl group, a 2,4-dichlorobenzoyl group, a 3,5-dichlorobenzoyl group, a diphenylacetyl group, a 1-naphthaleneacetyl group, a 2-naphthaleneacetyl group and like). These erythromycin A derivatives are prepared by treating erythromycin A with a corresponding carbonyl chloride, acyl chloride or acid anhydride according to a conventional manner.

When used the erythromycin A derivative which is not substituted at a hydrogen atom of the 2′-hydroxy group and at a methyl group of the 3′-dimethylamino group as a starting material, the introduction of the substituent groups as described above to the 2′- and/or 3′-positions of erythromycin A should be carried out in any desired sequence prior to the methylation using a corresponding carbonyl chloride, acyl chloride or acid anhydride according to a conventional manner.

As stated above, the present invention makes it possible to effect the selective methylation only of a hydroxy group at the 6-position of erythromycin A which was difficult in the past, and provides novel anti-bacterial agents or intermediates which make it easy to synthesize 6-O-methylerythromycin A being useful as anti-bacterial agents. For example, a 6-O-methylerythromycin A 9-oxime derivative can be subjected to deoximation to give a 6-O-methylerythromycin A derivative according to a conventional manner. If necessary, it can be carried out to eliminate the substituent groups of a hydrogen atom of the 2'-hydroxy group and/or a methyl group of the 3'-dimethylamino group, followed by N-methylation before or after the deoximation above.

Subsequently, the present invention will be more concretely illustrated by following Examples and Referential Example, but the invention is not limited thereto.

EXAMPLE 1

Preparation of 2'-O,3'-N-bis(benzyloxycarbonyl)-N-demethylerythromycin A 9-oxime.

To 300 ml of dry methanol were added 49.4 g of 2'-O,3'-N-bis(benzyloxycarbonyl)-N-demethylerythromycin A, 17.4 g of hydroxylamine hydrochloride and 18.73 g of imidazole, and the mixture was stirred at room temperature for 3 days. Most of the solvent was evaporated, the residue was poured into 700 ml of a saturated aqueous sodium bicarbonate solution, and the mixture was extracted twice with 500 ml of ethyl acetate. These ethyl acetate layers were combined, washed 3 times with 300 ml of a saturated aqueous sodium chloride solution, and dried over anhydrous magnesium sulfate. The solvent was evaporated to give a crude product, which was then recrystallized from a mixture of chloroform and petroleum ether to give 34.67 g of the title compound.

m.p. 149°–151° C.

Elemental analysis for $C_{52}H_{78}N_2O_{17}$; Calcd. (%): C 62.26, H 7.84, N 2.79; Found (%): C 61.97, H 7.58, N 2.72.

EXAMPLE 2

Preparation of 2'-O,3'-N-bis(benzyloxycarbonyl)-N-demethylerythromycin A 9-[O-(m-nitrobenzyl)oxime].

In 30 ml of acetone was dissolved 5 g of 2'-O,3'-N-bis(benzyloxycarbonyl)-N-demethylerythromycin A 9-oxime, 0.94 g of m-nitrobenzyl chloride and 0.362 g of 85% potassium hydroxide powder were added, and the mixture was stirred for 2 hours.

The solvent was evaporated under reduced pressure. To the residue was added 100 ml of a saturated aqueous sodium bicarbonate solution, and the mixture was extracted 3 times with 150 ml of ethyl acetate. The organic solvent layers were combined, washed with a saturated aqueous sodium chloride solution, and dried over anhydrous magnesium sulfate. The solvent was evaporated and the crude product thus obtained was purified by a silica gel column chromatography [Wako gel C-200 produced by Wako Junyaku Co., a mixture of benzene and ethyl acetate (3:1) as an eluant] to give 4.79 g of the title compound, which was then recrystallized from a mixture of ethyl acetate and n-hexane.

m.p. 108°–110° C.

By the similar procedure were obtained the following compounds.

2'-O,3'-N-bis(benzyloxycarbonyl)-N-demethylerythromycin A 9-[O-methyloxime]

m.p. 118°–121° C.

2'-O,3'-N-bis(benzyloxycarbonyl)-N-demethylerythromycin A 9-[O-ethyloxime]

m.p. 112°–114° C.

2'-O,3'-N-bis(benzyloxycarbonyl)-N-demethylerythromycin A 9-[O-isopropyloxime]

m.p. 103°–105° C.

2'-O,3'-N-bis(benzyloxycarbonyl)-N-demethylerythromycin A 9-[O-(p-methoxybenzyl)oxime]

m.p. 100°–102° C.

2'-O,3'-N-bis(benzyloxycarbonyl)-N-demethylerythromycin A 9-[O-(m-chlorobenzyl)oxime]

m.p. 99°–100° C.

2'-O,3'-N-bis(benzyloxycarbonyl)-N-demethylerythromycin A 9-[O-(1-naphthylmethyl)oxime]

m.p. 187°–189° C.

EXAMPLE 3

Preparation of 2'-O,3'-N-bis(benzyloxycarbonyl)-N-demethylerythromycin A 9-[O-(p-bromobenzyl) oxime].

In 80 ml of acetone was dissolved 20.0 g of 2'-O,3'-N-bis(benzyloxycarbonyl)-N-demethylerythromycin A 9-oxime, 6.0 g of p-bromobenzyl bromide and 1.23 g of 85% potassium hydroxide powder were added, and the mixture was stirred for 2 hours at room temperature.

Working up according to the procedure similar to that of Example 2, there was obtained the crude product, which was then recrystallized from a mixture of diethyl ether and petroleum ether to give 21.3 g of the title compound.

m.p. 100°–102° C.

By the similar procedure were obtained the following compounds.

2'-O,3'-N-bis(benzyloxycarbonyl)-N-demethylerythromycin A 9-[O-(n-propyl)oxime]

m.p. 109°–111° C.

2'-O,3'-N-bis(benzyloxycarbonyl)-N-demethylerythromycin A 9-[O-(p-chlorobenzyl)oxime]

m.p. 127°–130° C.

2'-O,3'-N-bis(benzyloxycarbonyl)-N-demethylerythromycin A 9-[O-(2,4-dichlorobenzyl)oxime]

m.p. 94.5°–96° C.

2'-O,3'-N-bis(benzyloxycarbonyl)-N-demethylerythromycin A 9-[O-(p-nitrobenzyl)oxime]

m.p. 119°–121° C.

EXAMPLE 4

Preparation of 2'-O,3'-N-bis(benzyloxycarbonyl)-N-demethylerythromycinA 9-[O-(methoxymethyl) oxime].

In 20 ml of tetrahydrofuran were dissolved 1 g of 2'-O,3'-N-bis(benzyloxycarbonyl)-N-demethylerythromycin A 9-oxime and 0.1 ml of methyl chloromethyl ether, 58 mg of 50% sodium hydride was added, and the mixture was stirred at room temperature for 15 minutes.

After completion of the reaction, the mixture was diluted with 100 ml of ethyl acetate, and 100 ml of water was added. The organic layer was separated, washed, in turn, with a saturated aqueous sodium bicarbonate solution and an aqueous sodium chloride solution, and dried over anhydrous magnesium sulfate. After evaporation of the solvent, the crude product thus obtained was purified by a silica gel column chromatography [Wako gel C-200, a mixture of benzene and acetone (10:1–5:1) as an eluent], and recrystallized from a mixture of acetone and n-hexane to give 590 mg of the title compound as crystals.

m.p. 101°–104° C.

By the similar procedure were obtained the following compounds.

2'-O,3'-N-bis(benzyloxycarbonyl)-N-demethylerythromycin A 9-[O-(methylthiomethyl)oxime]

m.p. 101°–104° C.

2'-O,3'-N-bis(benzyloxycarbonyl)-N-demethylerythromycin A 9-[O-(2,2,2-trichloroethoxymethyl)oxime]

m.p. 108°–111° C.

2'-O,3'-N-bis(benzyloxycarbonyl)-N-demethylerythromycin A 9-[O-(benzyloxymethyl)oxime]
m.p. 122°–124° C.

EXAMPLE 5

Preparation of 2'-O,3'-N-bis(benzyloxycarbonyl)-N-demethylerythromycin A 9-[O-benzyloxime].

In 150 ml of dry N,N-dimethylformamide were dissolved 20.06 g of 2'-O,3'-N-bis(benzyloxycarbonyl)-N-demethylerythromycin A 9-oxime and 3.37 g of benzyl chloride, 1.25 g of 60% sodium hydride was added, and the mixture was stirred for an hour. The reaction solution was poured into 600 ml of a saturated aqueous sodium bicarbonate solution. The mixture was extracted each one time with 300 ml of ethyl acetate and 200 ml of the same solvent. The ethyl acetate layer was washed 3 times with 300 ml of a saturated aqueous sodium chloride solution, and dried over anhydrous magnesium sulfate. The solvent was evaporated and the crude product thus obtained was purified by a silica gel column chromatography [Art. 7734 produced by Merck Co., a mixture of ethyl acetate and n-hexane (1:2–1:1) as an eluant] to give 17.92 g of the title compound, which was then further recrystallized from a mixture of ethyl acetate and petroleum ether.
m.p. 105°–107° C.

By the similar procedure were obtained the following compounds.

2'-O,3'-N-bis(benzyloxycarbonyl)-N-demethylerythromycin A 9-[O-benzhydryloxime]

2'-O,3'-N-bis(benzyloxycarbonyl)-N-demethylerythromycin A 9-[O-(2-methoxyethoxy)methyloxime]
m.p. 99°–104° C.

EXAMPLE 6

Preparation of 2'-O,3'-N-bis(benzyloxycarbonyl)-N-demethylerythromycin A 9-[O-(o-chlorobenzyl) oxime].

In 60 ml of N,N-dimethylformamide was dissolved 13 g of 2'-O,3'-N-bis(benzyloxycarbonyl)-N-demethylerythromycin A 9-oxime, 2.30 g of o-chlorobenzyl chloride and 0.941 g of 85% sodium hydroxide powder were added under ice-cooling, and the mixture was stirred for 2 hours.

After completion of the reaction, the mixture was poured into 400 ml of water, and the crystals which precipitated were collected by filtration and washed with water. The crystals were further washed with 100 ml of a 10% aqueous ethanol solution and dried to give 14.02 g of the title compound as crystals, which were further recrystallized from a mixture of ethyl acetate and n-hexane.
m.p. 111°–113° C.

EXAMPLE 7

Preparation of 2'-O,3'-N-bis(benzyloxycarbonyl)-N-demethylerythromycin A 9-[O-trityloxime].

In 2 ml of N,N-dimethylformamide was dissolved 1.0 g of 2'-O,3'-N-bis(benzyloxycarbonyl)-N-demethylerythromycin A 9-oxime, 1.0 g of trityl chloride and 1 ml of triethylamine were added, and the mixture was stirred at 80°–100° C. for 5 hours. After completion of the reaction, the mixture was poured into 300 ml of water and extracted with methylene chloride. The methylene chloride layer was washed with a saturated aqueous sodium chloride solution, and dried over anhydrous sodium sulfate. After evaporation of the solvent, the crude product thus obtained was purified by a silica gel column chromatography [Wako gel C-200, a mixture of ethyl acetate and n-hexane (1:2) as an eluant] to give 0.80 g of the title compound.
m.p. 126°–128° C.

EXAMPLE 8

Preparation of 2'-O,3'-N-bis(benzyloxycarbonyl)-N-demethylerythromycin A 9-oxime (the other oxime isomer of the compound obtained in Example 1).

The mother liquor obtained by recrystallization in Example 1 was concentrated to dryness under reduced pressure, and the residue thus obtained was applied onto a silica gel column chromatography [Wako-gel C-200, a mixture of ethyl acetate and n-hexane (2:1) as an eluant]. The fractions showing Rf value 0.21 by thin layer chromatography analysis [thin layer plate silica gel 60 $F_{254}$ produced Merck Co., a mixture of chloroform and methanol (20:1) as a developing solvent] were collected and concentrated to dryness under reduced pressure to give 3.0 g of the same as the title compound of Example 1.

Subsequently, the fractions showing Rf value 0.12 were collected, and concentrated to dryness under reduced pressure to give 540 mg of the title compound as a white foam.
m.p. 115°–130° C.

It was detected by thin layer chromatography analysis that a part of this compound was isomerized to the title compound of Example 1 in chloroform or by heating. Furthermore, it was difficult to purify this compound by recrystallization, and this compound did not show any clear melting point.

EXAMPLE 9

Preparation of 2'-O,3'-N-bis(benzyloxycarbonyl)-N-demethylerythromycin A 9-[O-benzyloxime] (the other oxime isomer of the title compound of Example 5).

In 1.5 ml of dry N,N-dimethylformamide were dissolved 250 mg of 2'-O,3'-N-bis(benzyloxycarbonyl)-N-demethylerythromycin A 9-oxime (the other oxime isomer of the title compound of Example 1) obtained in Example 8 and 65 mg of benzyl chloride, 25 mg of 85% potassium hydroxide powder was added, and the mixture was stirred under ice-cooling for 2 hours. The mixture was poured into 10 ml of water, extracted with ethyl acetate, washed with a saturated aqueous sodium chloride solution and dried over anhydrous magnesium sulfate. After evaporation of the solvent, the crude product thus obtained was applied onto a silica gel column chromatography [Wako gel C-200, a mixture of benzene and acetone (6:1) as an eluant].

The fractions showing Rf value 0.57 by thin layer chromatography analysis [thin layer plate 60 $F_{254}$ produced by Merck Co., a mixture of benzene and acetone (3:1) as a developing solvent], were collected and concentrated to dryness to give 50 mg of the same as the title compound of Example 5.

Subsequently, the fractions showing Rf value 0.48 were collected and concentrated to dryness under reduced pressure to give 150 mg of the title compound, which was then recrystallized from diethyl ether.
m.p. 144°–147° C.

It was detected by thin layer chromatography analysis that this compound did not change in chloroform or by heating.

EXAMPLE 10

Preparation of erythromycin A 9-[O-methyloxime] 2'-(3,4,5-trimethoxy)benzoate.

In 200 ml of acetone was dissolved 2.6 g of erythromycin A 9-[O-methyloxime], 1.72 g of 3,4,5-trimethoxybenzoyl chloride and 2.86 g of sodium bicarbonate were added, and the mixture was refluxed by heating for 11 hours. After completion of the reaction, the solvent was evaporated under reduced pressure. To the residue was added water, and the mixture was extracted with methylene chloride. The organic layer was washed with a saturated aqueous sodium chloride solution and dried over anhydrous magnesium sulfate.

Evaporation of the solvent under reduced pressure gave the crude product, which was then purified by silica gel column chromatography [Art. 7734 produced by Merck Co., a mixture of chloroform and acetone (4:1) as an eluant] to give 1.85 g of the title compound.
m.p. 127°–130° C.

EXAMPLE 11

(1) Preparation of 3'-N-benzyloxycarbonyl-N-demethylerythromycin A.

In 250 ml of methylene chloride was dissolved 29 g of N-demethylerythromycin A, and 27.8 ml of triethylamine and 7.5 g of benzyloxycarbonyl chloride were added under ice-cooling.

The mixture was stirred at 0°–5° C. for 5 hours, and concentrated to about 50 ml. To this was added 800 ml of water, the crystals which precipitated were collected by filtration to give 20 g of the title compound, which was then recrystallized from a mixture of ethyl acetate and n-hexane.
m.p. 157°–158° C.

(2) Preparation of 3'-N-benzyloxycarbonyl-N-demethylerythromycin A 9-oxime.

To 75 ml of anhydrous methanol were added 12.55 g of 3'-N-benzyloxycarbonyl-N-demethylerythromycin A obtained in the above item (1), 5.11 g of hydroxylamine hydrochloride and 5.5 g of imidazole, and the mixture was stirred at room temperature for 52 hours. Most of the solvent was evaporated, the residue was poured into 200 ml of a saturated aqueous sodium bicarbonate solution and extracted 3 times with 350 ml of ethyl acetate.

The ethyl acetate layers were combined, washed twice with 300 ml of a saturated aqueous sodium chloride solution and dried over anhydrous magnesium sulfate. The solvent was evaporated, and the crude product thus obtained was purified by a silica gel column chromatography [Wako gel C-200, a mixture of ethyl acetate and n-hexane (1:2–3:1) as an eluant] to give 8.6 g of the title compound, which was then recrystallized from a mixture of ethyl acetate and petroleum ether.
m.p. 169.5°–170.5° C.

EXAMPLE 12

Preparation of 3'-N-benzyloxycarbonyl-N-demethylerythromycin A 9-[O-benzyloxime].

In 30 ml of dry N,N-dimethylformamide were dissolved 4.79 g of 3'-N-benzyloxycarbonyl-N-demethylerythromycin A 9-oxime, 1.4 g of benzyl chloride and 0.92 g of potassium iodide, 0.55 g of 85% potassium hydroxide powder was added under ice-cooling, and the mixture was stirred for 2 hours.

The mixture was treated by the procedure similar to that of Example 6, the crude product thus obtained was purified by a silica gel column chromatography [Wako gel C-200, a mixture of benzene and acetone (40:1) as an eluant] to give 4.55 g of the title compound, which was then recrystallized from isopropyl alcohol.
m.p. 110°–113° C.

EXAMPLE 13

Preparation of 2'-O-benzyloxycarbonylerythromycin A 9-[O-benzyloxime].

To 10 ml of acetone were added 1.14 g of erythromycin A 9-[O-benzyloxime], 277 mg of benzyloxycarbonyl chloride and 137 mg of sodium bicarbonate, and the mixture was stirred at room temperature for 3 hours to carry out the reaction. After completion of the reaction, the acetone was evaporated, and the residue was extracted with ethyl acetate. The extract was washed, in turn, with a saturated aqueous sodium bicarbonate solution and a saturated aqueous sodium chloride solution, and dried over anhydrous magnesium sulfate. The solvent was evaporated, and the residue was purified by a silica gel column chromatography [Wako gel C-200, ethyl acetate as an eluant] and recrystallized from a mixture of diethyl ether and n-hexane to give 1.093 g of the title compound.
m.p. 155°–157° C.

EXAMPLE 14

Preparation of erythromycin A 9-[O-(o-chlorobenzyl)oxime].

1.498 g of erythromycin A 9-oxime, 354 mg of o-chlorobenzyl chloride and 168 mg of 85% potassium hydroxide powder in 100 ml of N,N-dimethylformamide were stirred together at room temperature for 1.5 hours to proceed the reaction.

Subsequently, the mixture was poured into 500 ml of ice-water, and extracted with ethyl acetate. The extract was washed with a saturated aqueous sodium chloride solution and dried over anhydrous magnesium sulfate. The solvent was evaporated and the residue was purified by a silica gel column chromatography [Wako gel C-200, ethyl acetate as an eluant] and recrystallized from n-hexane to give 1.562 g of the title compound.
m.p. 114°–117° C.

To a mixture of 5 g of the compound thus obtained and 5.77 g of sodium bicarbonate in 8.5 ml of dioxane were added 8.14 ml of benzyloxycarbonyl chloride by dropwise with stirring at 55°–65° C. The mixture was stirred at 65° C. for an hour. After completion of the reaction, 10 ml of dichloromethane was added to the reaction mixture. The resulting mixture was filtered and the filtrate was diluted with 80 ml of n-hexane to give 5.92 g of 2'-O,3'-N-bis(benzyloxycarbonyl)-N-demethylerythromycin A 9-[O-(o-chlorobenzyl)oxime] as crystal. This compound was identical with the compound obtained in Example 6 in terms of data of melting point, IR and NMR.

EXAMPLE 15

Preparation of 2'-O-benzyloxycarbonylerythromycin A 9-[O-(o-chlorobenzyl)oxime].

To 15 ml of acetone were added 1.5 g of erythromycin A 9-[O-(o-chlorobenzyl)oxime], 438 mg of benzyloxycarbonyl chloride and 216 mg of sodium bicarbonate. Subsequently the mixture was treated by the procedure similar to that of Example 13, the crystals thus obtained were recrystallized from a mixture of diethyl ether and n-hexane to give 1.248 g of the title compound.

m.p. 156°-160° C.

EXAMPLE 16

Preparation of 6-O-methyl-2'-O,3'-N-bis (benzyloxycarbonyl)-N-demethylerythromycin A 9-[O-methyloxime].

In 12 ml of a mixture of dimethyl sulfoxide and tetrahydrofuran (1:1) was dissolved 1.02 g of 2'-O,3'-N-bis(benzyloxycarbonyl)-N-demethylerythromycin A 9-[O-methyloxime]. To the solution were added 341 mg of methyl iodide and 100 mg of 85% potassium hydroxide powder, and the mixture was stirred at room temperature for 2 hours to carry out the reaction. After completion of the reaction, 100 ml of a saturated aqueous sodium bicarbonate solution was added, and the mixture was extracted each one time with 100 ml of ethyl acetate and with 50 ml of the same solvent. The ethyl acetate layer was washed 3 times with 100 ml of a saturated aqueous sodium chloride solution, and dried over anhydrous magnesium sulfate. The solvent was evaporated under reduced pressure, and the residue thus obtained was purified by a silica gel column chromatography [Wako gel C-200, a mixture of ethyl acetate and n-hexane (1:1) as an eluant] to give 0.82 g of the title compound as a white foam.

Elemental Analysis for $C_{54}H_{82}N_2O_{17}$; Calcd. (%): C 62.89, H 8.02, N 2.72; Found (%): C 62.48, H 7.93, N 2.65.

EXAMPLE 17

Preparation of 6-O-methyl-2'-O,3'-N-bis (benzyloxycarbonyl)-N-demethylerythromycin A 9-[O-ethyloxime].

Following the procedure similar to that of Example 16 and using 1.028 g of 2'-O,3'-N-bis(benzyloxycarbonyl)-N-demethylerythromycin A 9-[O-ethyloxime], 341 mg of methyl iodide and 100 mg of 85% potassium hydroxide powder in 12 ml of a mixture of dimethyl sulfoxide and tetrahydrofuran (1:1), there was obtained 1.05 g of the crude product, which was then recrystallized from a mixture of diethyl ether and n-hexane to give 0.85 g of the title compound as crystals.

m.p. 105°-108° C.

Elemental analysis for $C_{55}H_{84}N_2O_{17}$; Calcd. (%): C 63.20, H 8.10, N 2.68; Found (%): C 63.23, H 7.84, N 2.72.

EXAMPLE 18

Preparation of 6-O-methyl-2'-O,3'-N-bis (benzyloxycarbonyl)-N-demethylerythromycin A 9-[O-(n-propyl)oxime].

Following the procedure similar to that of Example 16 using 1.042 g of 2'-O,3'-N-bis(benzyloxycarbonyl)-N-demethylerythromycin A 9-[O-(n-propyl)oxime], 370 mg of methyl iodide and 100 mg of 85% potassium hydroxide powder in 12 ml of a mixture of dimethyl sulfoxide and tetrahydrofuran (1:1) for proceeding the reaction, there was obtained 1.13 g of the crude product, which was then purified by the same silica gel column chromatography in Example 16 to give 0.52 g of the title compound as a white foam.

Elemental analysis for $C_{56}H_{86}N_2O_{17}$; Calcd. (%): C 63.49, H 8.18, N 2.65; Found (%): C 63.53, H 8.10, N 2.75.

EXAMPLE 19

Preparation of 6-O-methyl-2'-O,3'-N-bis (benzyloxycarbonyl)-N-demethylerythromycin A 9-[O-isopropyloxime].

Following the procedure similar to that of Example 16 and using 0.44 g of 2'-O,3'-N-bis(benzyloxycarbonyl)-N-demethylerythromycin A 9-[O-isopropyloxime], 144 mg of methyl iodide and 41.8 mg of 85% potassium hydroxide powder in 6 ml of a mixture of dimethyl sulfoxide and tetrahydrofuran (1:1), the reaction was carried out. Working up according to a conventional manner followed by purification using the same silica gel column chromatography in Example 16, there was obtained 0.36 g of the title compound as a white foam.

Elemental analysis for $C_{56}H_{86}N_2O_{17}$; Calcd. (%): C 63.49, H 8.18, N 2.65; Found (%): C 63.39, H 7.86, N 2.72.

EXAMPLE 20

Preparation of 6-O-methyl-2'-O,3'-N-bis (benzyloxycarbonyl)-N-demethylerythromycin A 9-[O-(methoxymethyl)oxime].

To 10 ml of a mixture of dimethyl sulfoxide and tetrahydrofuran (1:1) were added 1.0 g of 2'-O,3'-N-bis(benzyloxycarbonyl)-N-demethylerythromycin A 9-[O-(methoxymethyl)oxime], 320 mg of methyl iodide and 95 mg of 85% potassium hydroxide powder, and the mixture was stirred at room temperature for 45 minutes in order to carry out the reaction. Working up according to the procedure similar to that of Example 16, there was obtained the crude product, which was then recrystallized from a mixture of acetone and n-hexane to give 705 mg of the title compound as crystals.

m.p. 197°-199° C.

Elemental analysis for $C_{55}H_{84}N_2O_{18}$; Calcd. (%): C 62.25, H 7.98, N 2.64; Found (%): C 62.25, H 7.99, N 2.75.

EXAMPLE 21

Preparation of 6-O-methyl-2'-O,3'-N-bis (benzyloxycarbonyl)-N-demethylerythromycin A 9-[O-(methylthiomethyl)oxime].

Following the procedure similar to that of Example 16 using 230 mg of 2'-O,3'-N-bis(benzyloxycarbonyl)-N-demethylerythromycin A 9-[O-(methylthiomethyl)oxime], 98 mg of methyl iodide and 20 mg of 85% potassium hydroxide powder in 4 ml of a mixture of dimethyl sulfoxide and tetrahydrofuran (1:1) for proceeding the reaction, followed by working up according to a conventional manner, there was obtained 230 mg of the crude product, which was then purified by a silica gel column chromatography (Wako gel C-200, methylene chloride as an eluant) to give 98 mg of the title compound as a white foam.

NMR (CDCl$_3$) δ : 2.23 (3H, —SCH$_3$), 3.07 (3H, 6—OCH$_3$), 5.08 (2H, —OCH$_2$S—).

EXAMPLE 22

Preparation of 6-O-methyl-2'-O,3'-N-bis (benzyloxycarbonyl)-N-demethylerythromycin A 9-[Obenzyloxime].

Following the procedure similar to that of Example 16 using 1.09 g of 2'-O,3'-N-bis(benzyloxycarbonyl)-N-demethylerythromycin A 9-[O-benzyloxime], 341 mg of methyl iodide and 99 mg of 85% potassium hydroxide powder in 12 ml of a mixture of dimethyl sulfoxide and tetrahydrofuran (1:1), the reaction was carried out. Working up followed by purification using a silica gel column chromatography, there was obtained 830 mg of the title compound as a white foam, which was then recrystallized from a mixture of diethyl ether and petroleum ether.

m.p. 154.5°–156° C.

Elemental analysis for $C_{60}H_{86}N_2O_{17}$; Calcd. (%): C 65.08, H 7.83, N 2.53; Found (%): C 64.76, H 7.83, N 2.53.

EXAMPLE 23

Preparation of 6-O-methyl-2'-O,3'-N-bis(benzyloxycarbonyl)-N-demethylerythromycin A 9-[O-(p-methoxybenzyl)oxime].

5.6 g of 2'-O,3'-N-bis(benzyloxycarbonyl)-N-demethylerythromycin A 9-[O-(p-methoxybenzyl)oxime], 1.7 g of methyl iodide and 995 mg of 85% potassium hydroxide powder in 60 ml of a mixture of dimethyl sulfoxide and tetrahydrofuran (1:1) were stirred for 3.5 hours for proceeding the reaction. Working up according the procedure similar to that of Example 16, there was obtained about 6 g of the crude product, which was then purified by a silica gel column chromatography [Wako gel C-200, a mixture of ethyl acetate and n-hexane (1:2) as an eluant] to give 4.3 g of the title compound as a white foam.

Elemental analysis for $C_{61}H_{88}N_2O_{18}$; Calcd. (%): C 64.41, H 7.80, N 2.46; Found (%): C 63.67, H 7.67, N 2.46.

EXAMPLE 24

Preparation of 6-O-methyl-2'-O,3'-N-bis (benzyloxycarbonyl)-N-demethylerythromycin A 9-[O-(pchlorobenzyl)oxime].

To 100 ml of a mixture of dimethyl sulfoxide and tetrahydrofuran (1:1) were added 8.3 g of 2'-O,3'-N-bis(benzyloxycarbonyl)-N-demethylerythromycin A 9-[O-(p-chlorobenzyl)oxime], 2.5 g of methyl iodide and 730 mg of 85% potassium hydroxide powder, and the mixture was stirred at room temperature for 2 hours for proceeding the reaction. Working up according to the procedure similar to that of Example 16, there was obtained the crude product, which was then purified by a silica gel column chromatography [Wako gel C-200, a mixture of benzene and acetone (50:1–25:1) as an eluant] to give 7.5 g of the title compound as a white foam.

Elemental analysis for $C_{60}H_{85}ClN_2O_{17}$; Calcd. (%): C 63.12, H 7.50, N 2,45; Found (%): C 62.96, H 7.40, N 2,49.

EXAMPLE 25

Preparation of 6-O-methyl-2'-O,3'-N-bis(benzyloxycarbonyl)-N-demethylerythromycin A 9[O-(mchlorobenzyl)oxime].

1.12 g of 2'-O,3'-N-bis(benzyloxycarbonyl)-N-demethylerythromycin A 9-[O-(m-chlorobenzyl)oxime], 320 mg of methyl iodide and 73 mg of 85% potassium hydroxide power in 12 ml of a mixture of dimethyl sulfoxide and tetrahydrofuran (1:1) were stirred together at room temperature for 2 hours for proceeding the reaction. Working up according to the procedure similar to that of Example 16, there was obtained the crude product, which was then purified by a silica gel column chromatorgraphy (Wako gel C-200, methylene chloride as an eluant) to give 1.13 g of the title compound as crystals.

m.p. 86°–94° C.

Elemental analysis for $C_{60}H_{85}ClN_2O_{17}$; Calcd. (%): C 63.12, H 7.50, N 2.45; Found (%): C 62.96, H 7.47, N 2.43.

EXAMPLE 26

Preparation of 6-O-methyl-2'-O,3'-N-bis(benzyloxycarbonyl)-N-demethylerythromycin A 9-[O-(ochlorobenzyl)oxime].

In 50 ml of N,N-dimethylformamide was dissolved 13 g of 2'-O,3'-N-bis(benzyloxycarbonyl)-N-demethylerythromycin A 9-[O-(o-chlorobenzyl)oxime], 2.1 g of methyl iodide and 0.827 g of 85% potassium hydroxide powder were added under ice-cooling, and the mixture was stirred for 5 hours. After completion of the reaction the mixture was poured into 400 ml of water, the crystals which precipitated were collected by filtration, washed with 100 ml of 10% aqueous ethanol solution, and dried. The crude product thus obtained was recrystallized from isopropyl alcohol to give 10.27 g of the title compound as crystals.

m.p. 191°–193° C.

Elemental analysis for $C_{60}H_{85}ClN_2O_{17}$; Calcd. (%): C 63.12, H 7.50, N 2.45; Found (%): C 63.10, H 7.39, N 2.52.

EXAMPLE 27

Preparation of 6-O-methyl-2'-O,3'-N-bis(benzyloxycarbonyl)-N-demethylerythromycin A 9-[O-(pbromobenzyl)oxime].

11.72 g of 2'-O,3'-N-bis(benzyloxycarbonyl)-N-demethylerythromycin A 9-[O-(p-bromobenzyl)oxime], 3.41 g of methyl iodide and 990 mg of 85% potassium hydroxide powder in 120 ml of a mixture of dimethyl sulfoxide and tetrahydrofuran (1:1) were stirred together at room temperature for an hour for proceeding the reaction. Working up according to the procedure similar to that of Example 16, there was obtained the crude product, which was then purified by a silica gel column chromatography [Wako gel C-200, a mixture of ethyl acetate and n-hexane (1:2) as an eluant] to give 10.45 g of the title compound as a white foam.

m.p. 98°–103° C.

Elemental analysis for $C_{60}H_{85}BrN_2O_{17}$; Calcd. (%): C 60.75, H 7.22, N 2.39; Found (%): C 60.92, H 7.02, N 2.37.

EXAMPLE 28

Preparation of 6-O-methyl-2'-O,3'-N-bis(benzyloxycarbonyl)-N-demethylerythromycin A 9-[O-(2,4-dichlorobenzyl)oxime].

To 48 ml of a mixture of dimethyl sulfoxide and tetrahydrofuran (1:1) were added 4.044 g of 2'-O,3'-N-bis(benzyloxycarbonyl)-N-demethylerythromycin A 9-[O-(2,4-dichlorobenzyl)oxime], 1.33 g of methyl iodide and 380 mg of 85% potassium hydroxide powder, and the mixture was stirred in order to carry out the reaction. Reacting for 45 hours followed by working up according to the procedure similar to that of Example 1, there was obtained the crude product, which was then recrystallized from a mixture of diethyl ether and n-hexane to give 3.5 g of the title compound as crystals.

m.p. 180°–181° C.

Elemental analysis for $C_{60}H_{84}Cl_2N_2O_{17}$; Calcd. (%): C 61.27, H 7.20, N 2.38; Found (%): C 61.34, H 7.04, N 2.45.

EXAMPLE 29

Preparation of 6-O-methyl-2'-O,3'-N-bis(benzyloxycarbonyl)-N-demethylerythromycin A 9-[O-benzhydryloxime].

940 mg of 2'-O,3'-N-bis(benzyloxycarbonyl)-N-demethylerythromycin A 9-[O-benzyhydryloxime] was reacted with 350 mg of methyl iodide and 92 mg of 85% potassium hydroxide in 12 ml of a mixture of dimethyl sulfoxide and tetrahydrofuran (1:1) with stirring for an hour. Working up according to the procedure similar to that of Example 16, there was obtained the crude product, which was then purified by a silica gel column chromatography [Wako gel C-200, a mixture of ethyl acetate and n-hexane (1:2) as an eluant] to give 620 mg of the title compound.

EXAMPLE 30

Preparation of 6-O-methyl-2'-O,3'-N-bis(benzyloxycarbonyl)-N-demethylerythromycin A 9-[O-trityloxime], To 4 ml of a mixture of dimethyl sulfoxide and tetrahydrofuran (1:1) were added 450 mg of 2'-O,3'-N-bis(benzyloxycarbonyl)-N-demethylerythromycin A 9-[O-trityloxime], 123 mg of methyl iodide and 30 mg of 85% potassium hydroxide powder, and the mixture was stirred for 3 hours to carry out the reaction. After completion of the reaction, working up according to the procedure similar to that of Example 16, there was obtained the crude product, which was then purified by a silica gel column chromatography (Wako gel C-200, methylene chloride as an eluant) to give 270 mg of the title compound.

EXAMPLE 31

Preparation of 6-O-methyl-2'-O,3'-N-bis(benzyloxycarbonyl)-N-demethylerythromycin A 9-[O-benzyloxime].

In 12 ml of a mixture of dimethyl sulfoxide and tetrahydrofuran (1:1) were dissolved 547 mg of 2'-O,3'-N-bis(benzyloxycarbonyl)-N-demethylerythromycin A 9-[O-benzyloxime] and 1.37 g of methyl iodide, 34 mg of 60% sodium hydride was added, and the mixture was stirred for an hour in order to carry out the reaction. Working up according to the procedure similar to that of Example 16, there was obtained the crude product, which was then purified by a silica gel column chromatography [Art. 7734 produced by Merck Co., a mixture of ethyl acetate and n-hexane (1:3) as an eluant] to give 383 mg of the title compound.

This compound was identical with the compound obtained in Example 22 in terms of data of melting point, IR and NMR.

EXAMPLE 32

Preparation of 6-O-methyl-2'-O,3'-N-bis(benzyloxycarbonyl)-N-demethylerythromycin A 9-[O-(o-chlorobenzyl)oxime].

In 12 ml of a mixture of dimethyl sulfoxide and tetrahydrofuran (1:1) was dissolved 1.1 g of 2'-O,3'-N-bis(benzyloxycarbonyl)-N-demethylerythromycin A 9-[O-(o-chlorobenzyl)oxime], 0.23 ml of dimethyl sulfate and 98 mg of 85% potassium hydroxide powder were added, and the mixture was stirred at room temperature for 90 minutes to carry out the reaction. Working up according to the procedure similar to that of Example 16, there was obtained the crude product, which was then purified by a silica gel column chromatography [Art. 7734 produced by Merck Co., methylene chloride as an eluant] to give 760 mg of the same as the compound obtained in Example 26.

EXAMPLE 33

Preparation of 6-O-methyl-2'-O,3'-N-bis(benzyloxycarbonyl)-N-demethylerythromycin A 9-[O-(m-nitrobenzyl)oxime].

In 20 ml of N,N-dimethylformamide was dissolved 2.97 g of 2'-O,3'-N-bis(benzyloxycarbonyl)-N-demethylerythromycin A 9-[O-(m-nitrobenzyl)oxime], 0.444 g of methyl iodide and 0.132 g of 95% sodium hydroxide powder were added under ice-cooling, and the mixture was stirred under cooling for 1.5 hours to carry out the reaction. After completion of the reaction, 70 ml of ethyl acetate was poured, and the resulting mixture was washed 5 times with 100 ml of a saturated aqueous sodium chloride solution and dried over anhydrous magnesium sulfate. The solvent was evaporated, and the residue was purified by a silica gel column chromatography [Wako gel C-200, a mixture of benzene and ethyl acetate (3:1) as an eluant] to give 2.023 g of the title compound as a white foam.

EXAMPLE 34

Preparation of 6-O-methyl-2'-O,3'-N-bis(benzyloxycarbonyl)-N-demethylerythromycin A 9-[O-(p-nitrobenzyl)oxime].

To 250 ml of a mixture of dimethyl sulfoxide and tetrahydrofuran (1:1) was added 20.2 g of 2'-O,3'-N-bis(benzyloxycarbonyl)-N-demethylerythromycin A 9-[O-(p-nitrobenzyl)oxime], 3.02 g of methyl iodide and 1.41 g of 85% potassium hydroxide powder were added under cooling, and the mixture was stirred for 1.5 hours to carry out the reaction. Furthermore, 2.52 g of methyl iodide and 0.586 g of 85% potassium hydroxide powder were added, and the mixture was stirred for 2 hours. After completion of the reaction, the working-up and purification similar to those of Example 33 gave 5.78 g of the title compound.

EXAMPLE 35

Preparation of 6-O-methyl-2'-O,3'-N-bis(benzyloxycarbonyl)-N-demethylerythromycin A 9-[O-(1-naphthylmethyl)oxime].

In 20 ml of N,N-dimethylformamide was dissolved 4g of 2'-O,3'-N-bis(benzyloxycarbonyl)-N-demethylerythromycin A 9-[O-(1-naphthylmethyl)oxime], 0.745 g of methyl iodide and 0.254 g of 85% potassium hydroxide powder were added under ice-cooling, and the mixture was stirred for 2 hours for proceeding the reaction. Following the procedure similar to that of Example 16, the crude product thus obtained was purified by a silica gel column chromatography [Wako gel C-200, a mixture of ethyl acetate and benzene (3:10) as an eluant] to give 2.21 g of the title compound, which was then recrystallized from isopropyl ether.

m.p. 193°–195° C.

Elemental analysis for $C_{64}H_{88}N_2O_{17}$; Calcd. (%): C 66.42, H 7.66, N 2.42; Found (%): C 66.56, H 7.67, N 2.48.

EXAMPLE 36

Preparation of 6-O-methyl-2'-O,3'-N-bis(benzyloxycarbonyl)-N-demethylerythromycin A 9-[O-(2-methoxyethoxymethyl)oxime].

In 94 ml of a mixture of dimethyl sulfoxide and 1,2-dimethoxyethane (1:1) were dissolved 8.58 g of 2'-O,3'-

N-bis(benzyloxycarbonyl)-N-demethylerythromycin A 9-[O-(2-methoxyethoxymethyl)oxime] and 5.38 g of methyl iodide, 1.04 g of 85% potassium hydroxide powder was added, and the mixture was stirred for an hour. Furthermore, 0.26 g of 85% potassium hydroxide powder was added and the mixture was stirred for an hour to carry out the reaction. After completion of the reaction, working up according to the procedure similar to that of Example 16, the crude product thus obtained was purified by a silica gel column chromatography [Art. 7734 produced by Merck Co., a mixture of chloroform and acetone (20:1) as an eluant] to give 6.15 g of the title compound as a white foam.

m.p. 87°–93° C.

Elemental analysis for $C_{57}H_{88}N_2O_{19}$; Calcd. (%): C 61.94, H 8.02, N 2.53; Found (%): C 62.21, H 7.81, N 2.56.

EXAMPLE 37

Preparation of 6-O-methyl-2'-O,3'-N-bis(benzyloxycarbonyl)-N-demethylerythromycin A 9-[O-(2,2,2-trichloroethoxymethyl)-oxime].

1.16 g of 2'-O,3'N-bis(benzyloxycarbonyl)-N-demethylerythromycin A 9-[O-(2,2,2-trichloroethoxymethyl)-oxime], 342 mg of methyl iodide and 100 mg of 85% potassium hydroxide powder in 10 ml of a mixture of dimethyl sulfoxide and tetrahydrofuran (1:1) were stirred together at room temperature for 1.5 hours for proceeding the reaction. Working up according to the procedure similar to that of Example 1, there was obtained the crude product, which was then purified by a silica gel column chromatography [Wako gel C-200, a mixture of benzene and acetone (50:1–10:1) as an eluant] and recrystallized from a mixture of acetone and n-hexane to give 860 mg of the title compound as prisms.

m.p. 110°–113° C.

Elemental analysis for $C_{56}H_{83}Cl_3N_2O_{18}$; Calcd. (%): C 57.07, H 7.10, N 2.38; Found (%): C 57.32 H 6.82, N 2.41.

Preparation of 6-O-methyl-2'-O,3'-N-bis(benzyloxycarbonyl)-N-demethylerythromycin A 9-[Obenzyloxymethyl)oxime].

In 100 ml of a mixture of dimethyl sulfoxide and tetrahydrofuran (1:1) was dissolved 12.9 g of 2'-O,3'-N-bis(benzyloxycarbonyl)-N-demethylerythromycin A 9-[O-(benzyloxymethyl)oxime], 3.92 g of methyl iodide and 1.14 g of 85% potassium hydroxide powder were added, and the mixture was stirred at room temperature for 40 minutes to carry out the reaction. After completion of the reaction, working up according to the procedure similar to that of Example 16, there was obtained the crude product, which was then purified by a silica gel column chromatography [Wako gel C-200, a mixture of benzene and acetone (100:1–12.5:1) as an eluant] and recrystallized from a mixture of isopropyl ether and n-hexane to give 9.35 g of the title compound as crystals.

m.p. 135°–136° C.

Elemental analysis for $C_{61}H_{88}N_2O_{18}$; Calcc. (%): C 64.42, H 7.80, N 2.46; Found (%): C 64.41, H 7.61, N 2.49.

EXAMPLE 39

Preparation of 6-O-methyl-2'-O,3'-N-bis(benzyloxycarbonyl)-N-demethylerythromycin A 9-[O-benzyloxime] (the other oxime isomer of the title compound of Example 22).

In 1.2 ml of a mixture of dimethyl sulfoxide and tetrahydrofuran (1:1) were reacted 130 mg of 2'-O,3'-N-bis(-benzyloxycarbonyl)-N-demethylerythromycin A 9-[O-benzyloxime] obtained in Example 9 (the other oxime isomer of the title compound of Example 5), 26 mg of methyl iodide and 10 mg of 85% potassium hydroxide powder according to the procedure similar to that of Example 16. Working up followed by purification using a silica gel column chromatography [Wako gel C-200, a mixture of ethyl acetate and n-hexane (1:2) as an eluant], there was obtained 102 mg of the title compound as a white foam.

m.p. 94°–99° C.

EXAMPLE 40

Preparation of 6-O-methylerythromycin A 9-[O-methyloxime]-2'-(3,4,5-trimethoxybenzoate).

In 6 ml of a mixture of dimethyl sulfoxide and 1,2-dimethoxyethane (1:1) was dissolved 580 mg of erythromycin A 9-[O-methyloxime]-2'-(3,4,5-trimethoxybenzoate), 136.8 mg of methyl iodide and 66 mg of 85% potassium hydroxide powder were added, and the mixture was stirred at room temperature for 2 hours to carry out the reaction. After completion of the reaction, 2 ml of triethylamine was added, and the mixture was extracted with ethyl acetate. The ethyl acetate layer was washed with a saturated aqueous sodium chloride solution and dried over anhydrous magnesium sulfate.

The solvent was evaporated under reduced pressure, and the crude product thus obtained was purified by a silica gel column chromatography [Art. 7734 produced by Merck Co., a mixture of chloroform and acetone (4:1) as an eluant] to give 260 mg of a title compound.

m.p. 131°–133° C.

EXAMPLE 41

Preparation of 6-O-methyl-3'-N-benzyloxycarbonyl-N-demethylerythromycin A 9-[O-benzyloxime].

In 3 ml of a mixture of dimethyl sulfoxide and tetrahydrofuran (1:1) was dissolved 335 mg of 3'-N-benzyloxycarbonyl-N-demethylerythromycin A 9-[O-benzyloxime], 75 mg of methyl iodide and 29 mg of 85% potassium hydroxide powder were added, and the mixture was stirred under ice-cooling for an hour to carry out the reaction. Working up according to the procedure similar to that of Example 16, the crude product thus obtained was purified by a silica gel column chromatography [Wako gel C-200, a mixture of benzene and acetone (40:1) as an eluant] to give 180 mg of the title compound.

m.p. 109°–114° C.

Further developing the chromatography, there was recovered 100 mg of 3'-N-benzyloxycarbonyl-N-demethylerythromycin A 9-[O-benzyloxime] of the starting material.

EXAMPLE 42

Preparation of 6-O-methyl-2'-O-benzyloxycarbonylerythromycin A 9-[O-benzyloxime].

Following the procedure similar to that of Example 16 using 487 mg of 2'-O-benzyloxycarbonylerythromycin A 9-[O-benzyloxime], 78.1 mg of methyl iodide and 30.8 mg of 85% potassium hydroxide powder in 5 ml of a mixture of dimethyl sulfoxide and tetrahydrofuran (1:1), the reaction was carried out. working up followed by purification using a silica gel column chromatography [Wako gel C-200, ethyl acetate as an eluant], there was obtained 405 mg of the title compound as a white foam.

$^1$H-NMR (CDCl$_3$) δ : 2.99 (3H, 6-OCH$_3$)

EXAMPLE 43

Preparation of 6-O-methyl-2'-O-benzyloxycarbonylerythromycin A 9-[O-(o-chlorobenzyl)oxime].

Following the procedure similar to that of Example 42 using 1.008 g of 2'-O-benzyloxycarbonylerythromycin A 9-[O-(o-chlorobenzyl)oxime], 185 mg of methyl iodide and 84 mg of 85% potassium hydroxide powder in 10 ml of a mixture of dimethyl sulfoxide and tetrahydrofuran (1:1) for proceeding the reaction, followed by purification, there was obtained 855 mg of the title compound as a white foam.

$^1$H-NMR (CDCl$_3$) δ : 2.98 (3H,6-OCH$_3$)

EXAMPLE 44

Preparation of 6-O-methyl-2'-O,3'-N-bis(benzyloxycarbonyl)-N-demethylerythromycin A 9-[O-methyloxime].

In 12 ml of a mixture of dimethyl sulfoxide and tetrahydrofuran (1:1) was dissolved 1.0 g of 2'-O,3'-N-bis(-benzyloxycarbonyl)-N-demethylerythromycin A 9-oxime, subsequently, 355 mg of methyl iodide and 145 mg of 85% potassium hydroxide powder were added, and the mixture was stirred at room temperature for 2 hours to carry out the reaction. After working-up according to a conventional manner, purification by a silica gel column chromatography [Wako gel C-200, a mixture of ethyl acetate and n-hexane (1:1) as an eluant] gave 0.8 g of the title compound. this compound was identical with the compound obtained in Example 16 in terms of data of IR and NMR.

REFERENCE EXAMPLE

In a solution of 11.4 g of 6-O-methyl-2'-O,3'-N-bis(-benzyloxycarbonyl)-N-demethylerythromycin A 9-[O-(o-chlorobenzyl)oxime] in 45 ml of methanol were added 2.85 g of 10% palladium carbon, 6 ml of formic acid and 1 g of sodium formate, and the mixture was stirred at room temperature for 5 hours. After completion of the reaction, the catalyst was filtered off. To the filtrate was added water, and the pH of the resulting solution was adjusted to about 10 with an aqueous sodium hydroxide solution. The crystals thus obtained were filtered, washed with water, dried and recrystallized from ethanol to give 5.6 g of 6-O-methyl-N-demethylerythromycin A 9-oxime.

m.p. 247°–249° C.

Elemental Analysis for C$_{37}$H$_{68}$N$_2$O$_{13}$; Calcd. (%): C 59.34, H 9.15, N 3.74; Found (%): C 59.35, H 8.87, N 3.78.

In a mixture of 12 ml of ethanol and 12 ml of water were dissolved 2 g of 6-O-methyl-N-demethylerythromycin A 9-oxime and 2.25 g of sodium hydrogen sulfite, and the solution was refluxed for 5 hours. After completion of the reaction, the reaction solution was poured into water, and the pH of the solution was adjusted to about 10 with an aqueous sodium carbonate solution. The mixture was extracted with dichloromethane, and the dichloromethane layer was washed with water, dried over anhydrous magnesium sulfate, concentrated under reduced pressure and recrystallized from a mixture of chloroform and diethyl ether to give 1.22 g of 6-O-methyl-N-demethylerythromycin A. m.p. 217°–219° C.

In a solution of 0.4 g of 6-O-methyl-N-demethylerythromycin A in 50 ml of methanol were added 0.2 g of 5% palladium carbon and 0.4 ml of 37% aqueous formaldehyde solution, and the mixture was stirred at room temperature under hydrogen atmosphere for 5 hours. After completion of the reaction, the catalyst was filtered off, and the filtrate was concentrated under reduced pressure. To the residue was added 50 ml of water, the pH of the solution was adjusted to about 10–10.3 with dilute aqueous sodium hydroxide solution, and the solution was extracted with dichloromethane. The dichloromethane layer was washed with water, dried over anhydrous magnesium sulfate and concentrated. The resulting crystals were recrystallized from ethanol to give 0.37 g of 6-O-methylerythromycin A.

What is claimed is:

1. A process for the selective methylation of a hydroxy group at the 6-position of an erythromycin A derivative which comprises converting an erythromycin A derivative into an erythromycin A 9-oxime derivative, and reacting the resulting erythromycin A 9-oxime derivative with a methylating agent.

2. A process according to claim 1, wherein the erythromycin A derivative is an erythromicin A having no substituent group or having conventional substituent groups in place of (1) a hydrogen atom of the 2'-hydroxy group or (2) a methyl group of the 3'-dimethylamino group or (3) both a hydrogen atom of the 2'-hydroxy group and a methyl group of the 3'-dimethylamino group.

3. A process according to claim 1, wherein the methylation is carried out in a solvent in the presence of a base.

4. A process according to claim 1, wherein the methylating agent is methyl iodide, methyl bromide, methyl chloride, dimethyl sulfate, methyl p-toluenesulfonate or methyl methanesulfonate.

5. A process according to claim 3, wherein the solvent is a polar aprotic solvent.

6. A process according to claim 5, wherein the polar aprotic solvent is dimethyl sulfoxide, N,N-dimethylformamide, hexamethylphosphoric triamide, a mixture consisting of two or more of these solvents, or a mixture consisting of one of these solvents and tetrahydrofuran or 1,2-dimethoxyethane.

7. A process according to claim 3, wherein the base is potassium hydroxide, sodium hydroxide, sodium hydride, or potassium hydride and, 1.0 to 1.7 molar equivalents of the base are used per mole of the erythromycin A 9-oxime derivative.

8. A process according to claim 1, wherein when the erythromycin A derivative having no substituent group in place of a hydrogen atom of the 2'-hydroxy group and a methyl groups of the 3'-dimethylamino group was used as a starting material, (1) a hydrogen atom of the 2'-hydroxy group or (2) of a methyl group of the 3'-dimethylamino group or (3) both a hydrogen atom of the 2'-hydroxy group and a methyl group of the 3'-dimethylamino group should be substituted by a conventional substituent group prior to the methylation.

* * * * *